United States Patent

Lorenz et al.

[11] 4,076,808
[45] Feb. 28, 1978

[54] O,S-DIALKYL-O-(N-METHOXY-BENZIMIDOYL)-THIONOTHIOL PHOSPHORIC ACID ESTERS AND ARTHROPODICIDAL USE

[75] Inventors: Walter Lorenz, Wuppertal; Ingeborg Hammann, Cologne, both of Germany

[73] Assignee: Bayer Aktiengesellschaft, Leverkusen, Germany

[21] Appl. No.: 721,725

[22] Filed: Sep. 9, 1976

[30] Foreign Application Priority Data

Oct. 10, 1975 Germany .............................. 2545392

[51] Int. Cl.² ........................... A01N 9/36; C07F 9/40
[52] U.S. Cl. ..................................... 424/211; 260/944
[58] Field of Search ......................... 260/944; 424/211

[56] References Cited
U.S. PATENT DOCUMENTS

| | | | |
|---|---|---|---|
| 3,597,506 | 8/1971 | Richter et al. | 260/944 |
| 3,760,041 | 9/1973 | Lorenz et al. | 260/944 |
| 3,792,130 | 2/1974 | Stach | 260/944 |

Primary Examiner—Richard L. Raymond
Attorney, Agent, or Firm—Burgess, Dinklage & Sprung

[57] ABSTRACT

O,S-Dialkyl-O-(N-methoxy-benzimidoyl)-thionothiol phosphoric acid esters of the formula

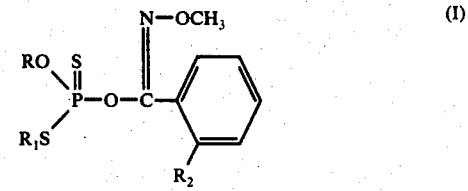

in which
R and $R_1$ each independently is alkyl with 1 to 4 carbon atoms, and
$R_2$ is hydrogen or nitro,
which possess arthropodicidal properties.

7 Claims, No Drawings

O,S-DIALKYL-O-(N-METHOXY-BENZIMIDOYL)-THIONOTHIOL PHOSPHORIC ACID ESTERS AND ARTHROPODICIDAL USE

The present invention relates to and has for its objects the provision of particular new O,S—dialkyl—O-(N-methoxy-benzimidoyl)-thionothiol phosphoric acid esters which possess arthropodical properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 3,760,041 that benzimidoylthionophosphoric acid esters, for example O,O-dimethyl- (Compound A) and O,O—diethyl—O—[N-methoxybenzimidoyl]-thionophosphoric acid esters (Compound B) and O,O—diethyl—O-[N-ethoxy-4-nitrobenzimidoyl]-thionophosphoric acid ester, (Compound C), are distinguished by an insecticidal and acaricidal activity.

The present invention now provides, as new compounds, the benzimidoylthionothiolphosphoric acid esters of the general formula

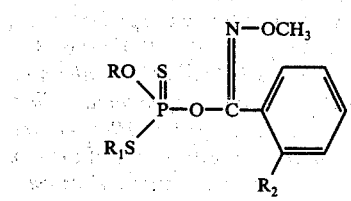

in which
R and $R_1$ each independently is alkyl with 1 to 4 carbon atoms, and
$R_2$ is hydrogen or nitro.

Preferably R is ethyl and $R_1$ is alkyl with 3 or 4 carbon atoms.

Surprisingly, the benzimidoylthionothiolphosphoric acid esters according to the invention exhibit a better insecticidal and acaricidal action than the corresponding known benzimidoylthionophosphoric acid esters of analogous structure and of the same type of action. The products according to the present invention thus represent a genuine enrichment of the art.

The present invention also provides a process for the preparation of a benzimidoylthionothiolphosphoric acid ester of the formula (I) in which an O,S-dialkylthionothiolphosphoric acid diester halide of the general formula

in which
R and $R_1$ have the above-mentioned meanings and
Hal represents halogen, preferably chlorine,
is reacted, if appropriate in the presence of a solvent or diluent, with an N-methoxybenzhydroxamic acid derivative of the general formula

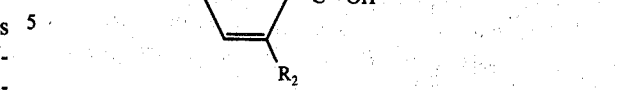

in which
$R_2$ has the above-mentioned meaning,
the latter being employed in the form of an alkali metal salt, alkaline earth metal salt or ammonium salt thereof or as such in the presence of an acid acceptor.

If, for example, O—ethyl—S—iso-propylthionothiolphosphoric acid diester choride and N-methoxy—2—nitro—benzhydroxamic acid are used as starting materials, the course of the reaction can be represented by the following equation:

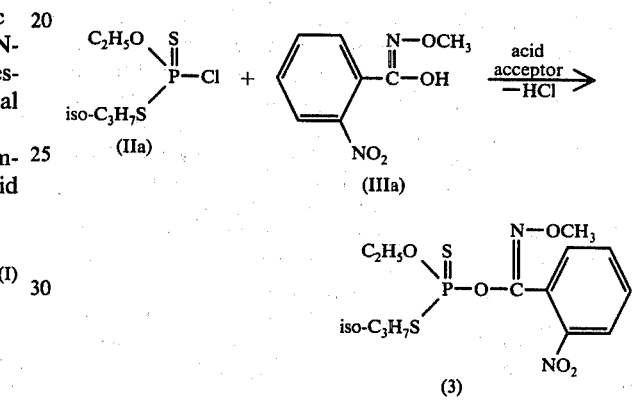

The O,S-dialkylthionothiolphosphoric acid diester halides (II) to be used as starting materials are known and can be prepared in accordance with customary processes, for example, USSR Patent Specification No. 184,863.

The following may be mentioned as individual examples: O,S—diethyl—, O—ethyl—S—n—propyl—, O—ethyl—S—isopropyl—, O—ethyl—S—n—butyl—, O—ethyl—S—isobutyl— and O—ethyl—S—sec.—butyl-thionothiolphosphoric acid diester chloride.

The N-methoxybenzhydroxamic acid derivatives (III) to be used as starting materials are also available in accordance with processes known from the literature, for example from the corresponding benzhydroxamic acids by reaction with alcoholic potassium hydroxide solution and alkyl iodide (see Waldstein, "Annalen" 181, 385) or from the corresponding benzoyl chlorides and alkoxylamine (see Gierke, "Annalen" 205, 278).

N—Methoxy— and N—methoxy—2—nitro-benzhydroxamic acid may be mentioned as examples.

The process for the preparation of th compounds according to the invention is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile. All customary acid-binding agents can be used as the acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example, triethylamine, trimethylamine, diemethylaniline, dimethylbenzylamine and pyridine.

The reaction temperature can be varied within a fairly wide range. In general, the reaction is carried out at between 0° and 120° C, preferably at 30° to 60° C.

The reaction is in general allowed to take place under normal pressure.

To carry out the process, the benzhydroxamic acid derivative (III) is preferably employed in 10 to 20% excess; it is first introduced, if appropriate together with an acid acceptor, into a solvent, and the thiophosphoric acid ester halide (II) is added dropwise to the mixture at the stated temperatures. After several hours' reaction at an elevated temperature, the batch is worked up in accordance with customary methods, either by pouring the cooled reaction mixture into water, whereupon a crystalline precipitate rapidly forms, and is then filtered off, or by extracting the aqueous phase with an organic solvent. After having been separated off, the organic layer is worked up in the generally customary manner by washing, drying and distilling off the solvent.

The new compounds are obtained in the form of oils which in some cases cannot be distilled without decomposition but which can be freed from the last volatile constituents by so-called "slight distillation", that is to say prolonged heating under reduced pressure to moderately elevated temperatures, and can be purified in this way. They are characterized by the refractive index.

As already mentioned, the benzimidoylthionothiolphosphoric acid esters according to the invention are distinguished by an arthropodicidal activity, especially by an excellent insecticidal and acaricidal activity. They are active against plant pests, pests harmful to health and pests of stored products. They possess a low phytotoxicity and a good action against both sucking and biting insects and against mites.

For this reason, the compounds according to the invention can be employed successfully as pesticides in plant protection as well as in the hygiene field and in the field of protection of stored products.

The active compounds are well tolerated by plants, have a favorable level of toxicity to warm-blooded animals, and can be used for combating arthropod pests, especially insects and arachnids which are encountered in agriculture, in forestry, in the protection of stored products and of materials, and in the hygiene field. They are active against normally sensitive and resistant species and against all or some stages of development.

The above-mentioned pests include: from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec;* from the class of the Symphyla, for example *Scutigerella immaculata;* from the class of the Thysanura, for example *Lepisma saccharina;* from the class of the Collembola, for example *Onychiurus armatus;* from the class of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.; from the order of the Anoplura, for example *Phyloxera vastatrix, Pemphigus* spp., *Pediculus humanus corporis, Haematopinus* spp. and *Linognathus* spp; from the order of the Mallophaga, for example *Trichodectes* spp. and *Damalinea* spp; from the order of the Thysanoptera, for example *Hercinothrips femoralis* and *Thrips tabaci;* from the order of the Heteroptera, for example *Eurygaster* spp., *Dysderdus intermedius, Piesma quadrata, Cimex lectularius, Rhodnius prolixus* and *Triatoma* spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kühniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp. *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example *Diprion* spp., *Hoplocampa* spp., *Lasius* spp., *Monomorium pharaonis* and *Vespa* spp.; from the order of the Diptera, for example, *Aëdes* spp., *Anopheles* spp., *Culex* spp., *Drosophila melanogaster, Musca* spp., *Fannia* spp., *Calliphora erythrocephala, Lucilia* spp. *Chrysomyia* spp. *Cuterebra* spp., *Gastrophilus* spp. *Hyppobosca* spp. *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the Siphonaptera, for example *Xenopsylla cheopis* and *Ceratophyllus* spp.; from the class of the Arachnida, for example *Scorpio maurus* and *Latrodectus mactans;* and from the order of the Acarina, for example *Acarus siro, Argas* spp.; *Ornithodoros* spp., *Dermanyssus gallinae, Eriophyes ribis, Phyllocoptruta oleivora, Boophilus* spp. *Rhipicephallus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., and *Tetranychus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorrilonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides and acaricides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Cabbage leaves (Brassica oleracea) were sprayed with the preparation of the active compound until dew moist and were then infested with caterpillars of the diamondback moth (Plutella maculipennis).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 1

(Plutella test)

| Active compound | Active compound concentration in % | Degree of destruction in % after 3 days |
|---|---|---|
| 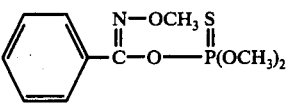 (known) (A) | 0.1<br>0.01 | 100<br>0 |
| 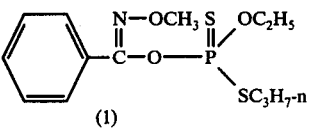 (1) | 0.1<br>0.01 | 100<br>100 |
| 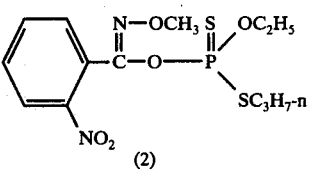 (2) | 0.1<br>0.01 | 100<br>100 |

EXAMPLE 2

Myzus test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 2

(Myzus test)

| Active compound | Active compound concentration in % | Degree of destruction in % after 1 day |
|---|---|---|
| 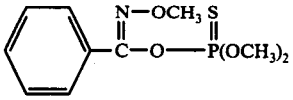 (known) (A) | 0.1<br>0.01<br>0.001 | 100<br>30<br>0 |
| 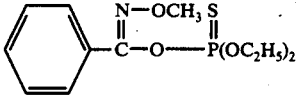 (known) (B) | 0.1<br>0.01<br>0.001 | 100<br>90<br>0 |
| 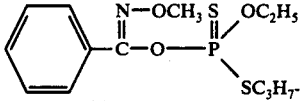 (1) | 0.1<br>0.01<br>0.001 | 100<br>100<br>90 |
| 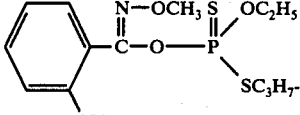 (2) | 0.1<br>0.01<br>0.001 | 100<br>99<br>70 |

EXAMPLE 3

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) were sprayed with the preparation of the active compound until dripping wet. These bean plants were heavily infested with the two-spotted spider mite (Tetranychus urticae) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 3

(*Tetranychus* test/resistant)

| Active compound | Active compound concentration in % | Degree of destruction in % after 2 days |
|---|---|---|
| (known) (A) — N=OCH₃, C-O-P(OCH₃)₂, S | 0.1 | 0 |
| (known) (B) — N=OCH₃, C-O-P(OC₂H₅)₂, S | 0.1 | 0 |
| (known) (C) — O₂N-C₆H₄-C(=N-OC₂H₅)-O-P(OH₂H₅)₂, S | 0.1 | 0 |
| (1) — N=OCH₃, C-O-P(OC₂H₅)(SC₃H₇-n), S | 0.1 | 100 |
| (2) — same with NO₂ on ring | 0.1 | 99 |

The process of this invention is illustrated by the following preparative Examples.

EXAMPLE 4 a. The N-methyloxy-2-nitro-benzhydroxamic acid

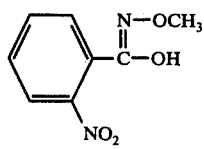

to be used as the starting material could be prepared, for example, as described below:

186 g (2.2 moles) of O-methylhydroxylamine hydrochloride, dissolved in 322 ml of water, were added dropwise at 10° C to 322 g (2.32 moles) of potassium carbonate dissolved in 276 ml of water, and 340 g (1.84 moles) of 2-nitrobenzoyl chloride were added dropwise to this mixture. After stirring for one hour, the precipitate which had separated out was filtered off and was suspended in lukewarm water in order to dissolve the potassium chloride with which it was mixed. The residue was again filtered off and washed with water. 192 g (53% of theory) of the compound of the above formula were obtained as a slightly granular, beige-colored powder of melting point 104° C (recrystallizable from ethyl acetate).

b) 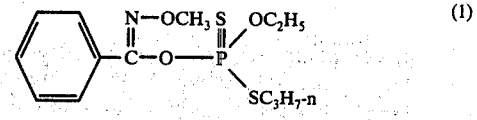 (1)

A mixture of 45.3 g (0.3 mole) of N-methoxybenzhydroxamic acid in 190 ml of acetonitrile and 49 g (0.36 mole) of potassium carbonate was stirred for 30 minutes at 50° C and thereafter 56.6 g (0.26 mole) of O-ethyl-S-n-propylthionothiolphosphoric acid diester chloride were added, whereupon the internal temperature rose to 37° C. After stirring for 20 hours at 50° C, the reaction batch was cooled and poured into water, and the oil which had separated out was taken up in toluene. The organic phase was washed with water, twice with 2 N sodium hydroxide solution and finally again with water until it reacted neutral. It was dried, the solvent was removed under reduced pressure and the residue was subjected to slight distillation. 70 g (85% of theory) of O—ethyl—S—n—propyl—O—(N-methoxy-benzimidoyl)—thionothiolphosphoric acid ester were obtained as a yellowish, clear oil having a refractive index $n_D^{23}$ of 1.5439.

EXAMPLE 5

O—Ethyl—S—n—propyl—O—(N—methoxy—2—nitrobenzimidoyl)-thionothiolphosphoric acid ester of the formula

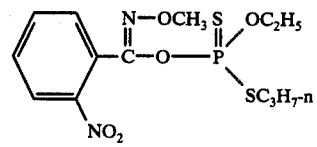 (2)

was obtained by a procedure analogous to that of Example 4, in 79.5% yield, and with a refractive index $n_D^{23}$ of 1.5495.

It will be appreciated that the instant specification and examples are set forth by way of illustration and not limitation, and that various modifications and changes may be made without departing from the spirit and scope of the present invention.

What is claimed is:

1. An O,S-dialkyl-O-(N-methoxy-benzimidoyl)-thionothiolphosphoric acid ester of the formula

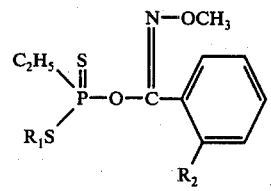

in which $R^1$ is alkyl with 3 or 4 carbon atoms, and
$R^2$ is hydrogen or nitro.

2. The compound according to claim 1 wherein such compound is O—ethyl—S—n—propyl—O—(N-methoxy-benzimidoyl)-thionothiolphosphoric acid ester of the formula

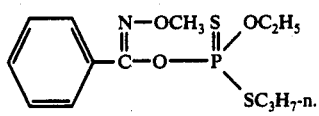

3. The compound according to claim 1 wherein such compound is O—ethyl—S—n—propyl—O—(N-methoxy—2—nitrobenzimidoyl)—thionothiolphosphoric acid ester of the formula

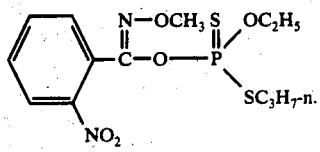

4. An arthropodicidall composition containing as active ingredient an arthropodicidally effective amount of a compound according to claim 2 in admixture with a diluent.

5. An arthropodicidal composition containing as active ingredient an arthropodicidally effective amount of a compound according to claim 3 in admixture with a diluent.

6. A method of combating arthropods, which comprises applying to the arthropods, or to a habitat thereof, an arthropodicidally effective amount of a compound according to claim 2.

7. A method of combating arthropods, which comprises applying to the arthropods, or to a habitat thereof, an arthropodicidally effective amount of a compound according to claim 3.

* * * * *